(12) United States Patent
Tanishima et al.

(10) Patent No.: US 9,743,842 B2
(45) Date of Patent: Aug. 29, 2017

(54) BIOLOGICAL PARAMETER DISPLAYING APPARATUS

(75) Inventors: Masami Tanishima, Tokyo (JP); Mitsushi Hyogo, Tokyo (JP)

(73) Assignee: NIHON KOHDEN CORPORATION, Tokyo (JP)

(*) Notice: Subject to any disclaimer, the term of this patent is extended or adjusted under 35 U.S.C. 154(b) by 395 days.

(21) Appl. No.: 12/910,088

(22) Filed: Oct. 22, 2010

(65) Prior Publication Data

US 2011/0098540 A1 Apr. 28, 2011

(30) Foreign Application Priority Data

Oct. 22, 2009 (JP) ................................ 2009-243125
Jul. 28, 2010 (JP) ................................ 2010-169504

(51) Int. Cl.
*A61B 5/0205* (2006.01)
*A61B 5/00* (2006.01)
(Continued)

(52) U.S. Cl.
CPC ............ *A61B 5/0205* (2013.01); *A61B 5/412* (2013.01); *A61B 5/742* (2013.01); *A61B 5/7445* (2013.01);
(Continued)

(58) Field of Classification Search
USPC ....................................................... 600/300
See application file for complete search history.

(56) References Cited

U.S. PATENT DOCUMENTS 5,103,828 A * 4/1992 Sramek .................. A61B 5/021
600/481
5,655,530 A 8/1997 Messerschmidt
(Continued)

FOREIGN PATENT DOCUMENTS

JP 10-31511 A 2/1998
JP 11-212630 A 8/1999
(Continued)

OTHER PUBLICATIONS

Abstract: Br J Biomed Sci. 2003;60(2):92-6m Sepstrup et al., "Change from dual- to single-platform reporting of CD4/CD8 values: experience from a small district general hospital laboratory." Br J Biomed Sci. 2003;60(2):92-6.*
(Continued)

*Primary Examiner* — Michael Kahelin
*Assistant Examiner* — Mitchell E Alter
(74) *Attorney, Agent, or Firm* — Pearne & Gordon LLP

(57) ABSTRACT

A biological parameter displaying apparatus includes: a coordinate displaying unit which displays first coordinates in which a first biological parameter of a patient, which is measured by a first measuring unit, is set as an X-axis, and a second biological parameter of the patient, which is different in kind from the first biological parameter and which is measured by a second measuring unit, is set as a Y-axis; a plot data producing unit which produces first plot data, each of the first plot data being produced based on first measurement values of the first and second biological parameters which are measured at a same time or in a same time zone; and a plot displaying unit which plots the first plot data in the first coordinates.

17 Claims, 10 Drawing Sheets

(51) Int. Cl.
*G06F 19/00* (2011.01)
*A61B 5/021* (2006.01)
*A61B 5/029* (2006.01)

(52) U.S. Cl.
CPC ...... *G06F 19/3406* (2013.01); *G06F 19/3456* (2013.01); *A61B 5/021* (2013.01); *A61B 5/029* (2013.01)

(56) References Cited

U.S. PATENT DOCUMENTS

| | | | |
|---|---|---|---|
| 5,697,959 A * | 12/1997 | Poore | 607/32 |
| 7,542,795 B2 | 6/2009 | Brodnick | |
| 2002/0147403 A1* | 10/2002 | Ogura | A61B 5/0285 600/500 |
| 2003/0004423 A1 | 1/2003 | Lavie et al. | |
| 2003/0083582 A1 | 5/2003 | Hirsh | |
| 2004/0167414 A1 | 8/2004 | Tanabe et al. | |
| 2006/0025698 A1 | 2/2006 | Nakagawa et al. | |
| 2006/0106322 A1 | 5/2006 | Arand et al. | |
| 2007/0027398 A1 | 2/2007 | Brodnick | |
| 2007/0142923 A1* | 6/2007 | Ayre | A61M 1/101 623/31 |
| 2008/0033306 A1* | 2/2008 | Joeken | A61B 5/029 600/485 |
| 2008/0139958 A1 | 6/2008 | Uemura et al. | |
| 2009/0099424 A1* | 4/2009 | O'Brien et al. | 600/301 |
| 2009/0124867 A1* | 5/2009 | Hirsh | A61M 5/142 600/301 |
| 2009/0216138 A1* | 8/2009 | Arand et al. | 600/508 |
| 2011/0021936 A1* | 1/2011 | Luo | 600/523 |
| 2011/0040713 A1 | 2/2011 | Colman et al. | |
| 2011/0087116 A1 | 4/2011 | Parkin et al. | |

FOREIGN PATENT DOCUMENTS

| | | |
|---|---|---|
| JP | 2004-21712 A | 1/2004 |
| JP | 2004-195204 A | 7/2004 |
| JP | 2005-507701 A | 3/2005 |
| JP | 2005-92853 A | 4/2005 |
| JP | 3656642 B2 | 5/2005 |
| JP | 2006-34803 A | 2/2006 |
| JP | 2007-222669 A | 9/2007 |
| JP | 2003-532456 | 2/2008 |
| JP | 2008-29793 A | 2/2008 |
| JP | 4327243 B1 | 9/2009 |
| JP | 2010-172365 A | 8/2010 |
| WO | 2009/063446 A2 | 5/2009 |
| WO | 2009/094700 A1 | 8/2009 |

OTHER PUBLICATIONS

Extended European Search Report for EP 10 18 8548 dated Feb. 10, 2011.

Forrester, J. S. et al.: "Correlative Classification of Clinical and Hemodynamic Function After Acute Myocardial Infarction.", The American Journal of Cardiology, Feb. 1997, vol. 39, No. 2, Feb. 1977, pp. 137-145.

Japanese Office Action for the related Japanese Patent Application No. 2010-169504 dated Dec. 17, 2013.

Chinese Office Action for the related Chinese Patent Application No. 201010527804.9 dated Nov. 26, 2013.

Japanese Office Action for the related Japanese Patent Application No. 2010-169504 dated Aug. 9, 2013.

Chinese Office Action for the related Chinese Patent Application No. 201010527804.9 dated Jul. 16, 2014.

* cited by examiner

Realted Art

BIOLOGICAL PARAMETER DISPLAYING APPARATUS

BACKGROUND OF THE INVENTION

The present invention relates to a biological parameter displaying apparatus which automatically plots data related to two biological parameters (particularly cardiovascular parameters such as the blood pressure and the cardiac output) of different kinds that are acquired from a living body at the same time or in the same time zone, in XY coordinates, and which can display the data in the form of a trend display so as to clarify the plotted time sequence.

In order to know the trend of the circulatory dynamics, there is an apparatus which performs a trend display such as shown in FIG. 8. A trend display is a display in which the ordinate shows the values of biological parameters, and the abscissa shows the time. In the trend display of FIG. 8, temporal changes of biological parameters in the medium and long term can be easily known, thereby providing beneficial information to the a medical person.

As a graph showing a relationship between two different biological parameters, there are a cardiac function curve and the Forrester classification in which data related to two biological parameters acquired from a living body are displayed in XY coordinates.

In a cardiac function curve, the cardiac index CI is set as the Y-axis (ordinate), the pulmonary artery wedge pressure PCWP is set as the X-axis (abscissa), and data are plotted in XY coordinates as shown in FIG. 7. From the drawn curve, a medical person can easily know the circulatory dynamics such as whether the cardiac function is normal, decreased, or enhanced.

In the Forrester classification, similarly as shown in FIG. 7, for example, XY coordinates in which a cardiac function curve is displayed is divided into four events, and the events are classified as "I Normal", "II Mild", "III Low cardiac output", and "IV Low cardiac output+pulmonary congestion", respectively. Depending on the position where the data (indicated by the circles) of the patient are plotted, a medical person can easily know the circulatory dynamics such as a pathological condition due to cardiogenic shock.

In the trend display which is shown in FIG. 8, the abscissa is the time axis, and hence only temporal changes of parameters are known, so that the circulatory dynamics based on the linking of two different biological parameters cannot be known.

A graph such as shown in FIG. 7 is usually produced by first independently measuring two different biological parameters, and then plotting the data to form the graph. It cannot be always said that such a graph is produced by plotting data of two different biological parameters having appropriate temporal relationships.

The reason of this is as follows. In the case where the cardiac index CI and pulmonary artery wedge pressure PCWP shown in FIG. 7 are measured, an invasive technique in which a pulmonary artery catheter having a balloon at the tip end is inserted into the heart of the patient is employed. Moreover, the cardiac index CI is a value which is acquired by performing division on the cardiac output CO. In order to acquire the cardiac output CO, it is necessary to perform the thermodilution method or dye dilution method in which a medical person injects a predetermined solution into the patient in each measurement. Moreover, the pulmonary artery wedge pressure PCWP is a blood pressure in the case where the balloon at the tip end of the pulmonary artery catheter is inflated. In order to acquire the pulmonary artery wedge pressure PCWP, therefore, a medical person must inflate the balloon in each measurement. Therefore, data of the ordinate and the abscissa which are acquired by operations conducted by a medical person cannot be continuously measured.

Recently, an apparatus which can continuously calculate the cardiac output CO has been developed. In order to plot data in coordinates with temporal simultaneousness, however, a plurality of medical persons must respectively perform measurements, or a single medical person must simultaneously perform the measurements. Therefore, it cannot be said that the workability is high.

In the case where a graph such as shown in FIG. 7 is applied as a trend display of, for example, the circulatory dynamics of a living body, particularly, plotting must be performed while further considering the temporal simultaneousness of two different biological parameters. Even if simultaneous measurements are performed and data can be plotted in coordinates, the display is shown in the form indicating the time sequence. Although a technique in which the time is directly written as in FIG. 7 may be considered, there is a problem in display such as that, when the number of data to be plotted is increased, the data are hardly readable.

U.S. Pat. No. 7,542,795 and Japanese Patent No. 3,656,642 disclose art in which two different biological parameters are displayed in coordinates.

In U.S. Pat. No. 7,542,795, results of measurements by one electrocardiogram sensor are plotted in the ordinate and the abscissa. In Japanese Patent No. 3,656,642, the maximal and minimal blood pressures which are results of measurements by one blood pressure sensor are plotted in the ordinate and the abscissa. In the above art, it cannot be said that the measurements results are two different parameters, and the circulatory dynamics based on the linking of two different biological parameters cannot be known.

SUMMARY

It is therefore an object of the invention to provide a biological parameter displaying apparatus which automatically plots data related to two biological parameters that are acquired by different sensors from a living body at the same time or in the same time zone, in XY coordinates, and which can display the data in the form of a trend display so as to clarify the plotted time sequence.

In order to achieve the object, according to the invention, there is provided a biological parameter displaying apparatus comprising: a coordinate displaying unit which displays first coordinates in which a first biological parameter of a patient, which is measured by a first measuring unit, is set as an X-axis, and a second biological parameter of the patient, which is different in kind from the first biological parameter and which is measured by a second measuring unit, is set as a Y-axis; a plot data producing unit which produces first plot data, each of the first plot data being produced based on first measurement values of the first and second biological parameters which are measured at a same time or in a same time zone; and a plot displaying unit which plots the first plot data in the first coordinates.

The first plot data may include at least two data including first data and second data, the first data may be subsequent to the second data, and the first data and the second data may be displayed at a time interval.

The first data may be a latest data.

The first measurement values of the first and second biological parameters may be representative values of the first and second biological parameters, which are acquired from groups of values of the first and second biological parameters measured at the same time or in the same time zone.

The representative values may be one of median, mean, and mode values of the groups of the values of the first and second biological parameters measured at the same time or in the same time zone.

The first plot data may be plotted in a manner showing a time sequence.

The first plot data may include first, second and third data, and the second data is subsequent to the third data, and the first data is subsequent to the second data and is a latest data. In the manner showing the time sequence, a brightness of the first data may be highest, and a brightness of the second data may be identical to a brightness of the third data or a brightness of the second data may be higher than a brightness of the third data.

The first plot data may include first, second and third data, and the second data is subsequent to the third data, and the first data is subsequent to the second data and is a latest data. In the manner showing the time sequence, a size of the first data may be largest, and a size of the second data may be identical to a size of the third data or a size of the second data may be larger than a size of the third data.

The first plot data may include first and second data, and the first data is subsequent to the second data. In the manner showing the time sequence, a color of the first data may be different from a color of the second data.

The first plot data may include first and second data, and the first data is subsequent to the second data. In the manner showing the time sequence, the first data and the second data may be connected to each other by an arrow or a line.

When a distance between the first data and the second data is shorter than a length, the first data and the second data may not be connected to each other by the arrow or the line.

The first plot data may include first and second data, and the first data is subsequent to the second data and is a latest data. In the manner showing the time sequence, a shape of the first data may be different from a shape of the second data.

The first plot data may include first and second data, and the first data is subsequent to the second data and is a latest data. In the manner showing the time sequence, the first data may blink and the second data may not blink.

The first plot data may include first and second data, and the first data is subsequent to the second data. In the manner showing the time sequence, when the first data and the second data are overlapped with each other at least in part, the first data may be displayed on the second data.

The biological parameter displaying apparatus may further include a determination criterion displaying unit which displays information indicating whether the first plot data are normal or abnormal as a state of the patient.

The biological parameter displaying apparatus may further include a region displaying unit which displays a region showing whether the first plot data are adequate or critical as a state of the patient.

The first biological parameter may be a cardiovascular parameter which is one of a first parameter indicating a cardiac output/cardiac function which can be continuously measured and a second parameter indicating a preload/afterload of a heart which can be continuously measured, and the second biological parameter may be a cardiovascular parameter which is the other of the first and second parameters.

The patient may include a plurality of patients.

The biological parameter displaying apparatus may further include a time selecting unit which selects a time. The first plot data corresponding to the selected time may be plotted.

The coordinate displaying unit may display second coordinates in which a third biological parameter, which is measured by a third measuring unit, is set as an X-axis, and the second biological parameter is set as a Y-axis, the plot data producing unit may produce second plot data, each of the second plot data being produced based on second measurement values of the second and third biological parameters which are measured at a same time or in a same time zone, and the plot displaying unit may plot the second plot data in the second coordinates.

The coordinate displaying unit may display second coordinates in which a third biological parameter, which is measured by a third measuring unit, is set as an X-axis, and a fourth biological parameter, which is measured by a fourth measuring unit, is set as a Y-axis, the plot data producing unit may produce second plot data, each of the second plot data being produced based on second measurement values of the third and fourth biological parameters which are measured at a same time or in a same time zone, and the plot displaying unit may plot the second plot data in the second coordinates.

DETAILED DESCRIPTION OF EMBODIMENTS

Figure 1:
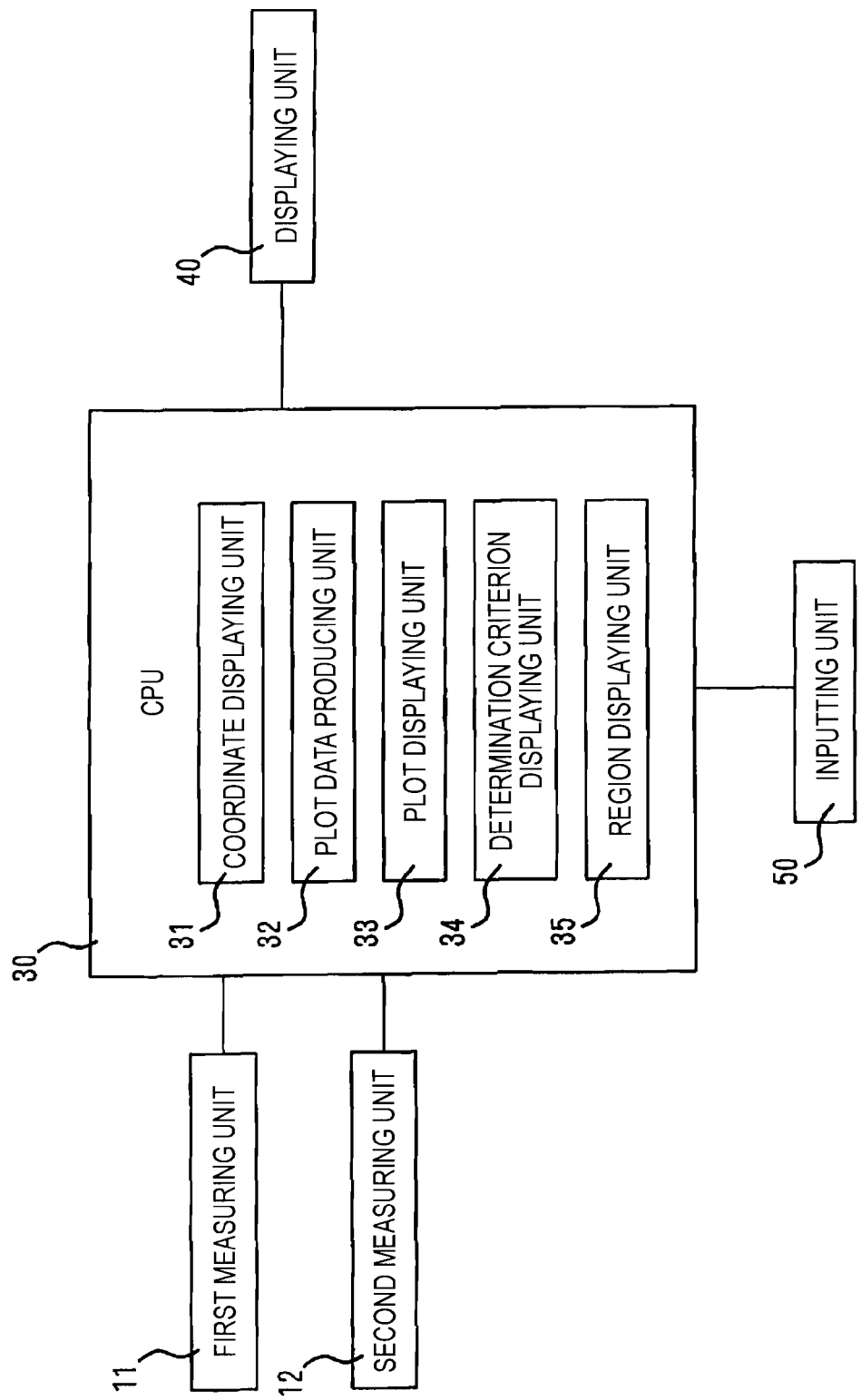
FIG. 1 is a block diagram showing the configuration of an embodiment of the biological parameter displaying apparatus of the invention.
Figure 2:
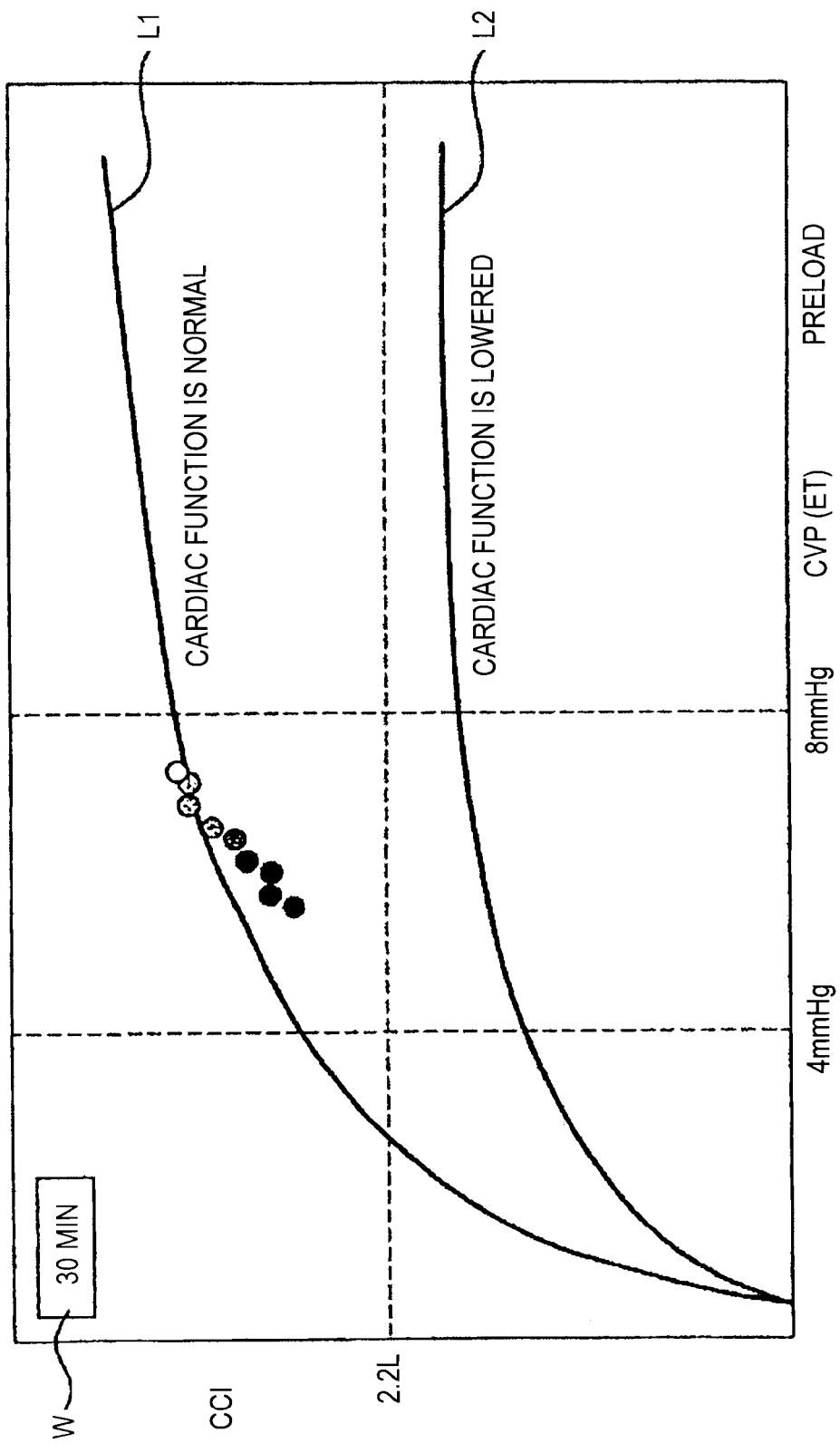
FIG. 2 is a view showing an example of an image which is displayed in the embodiment of the biological parameter displaying apparatus of the invention.
Figure 3:
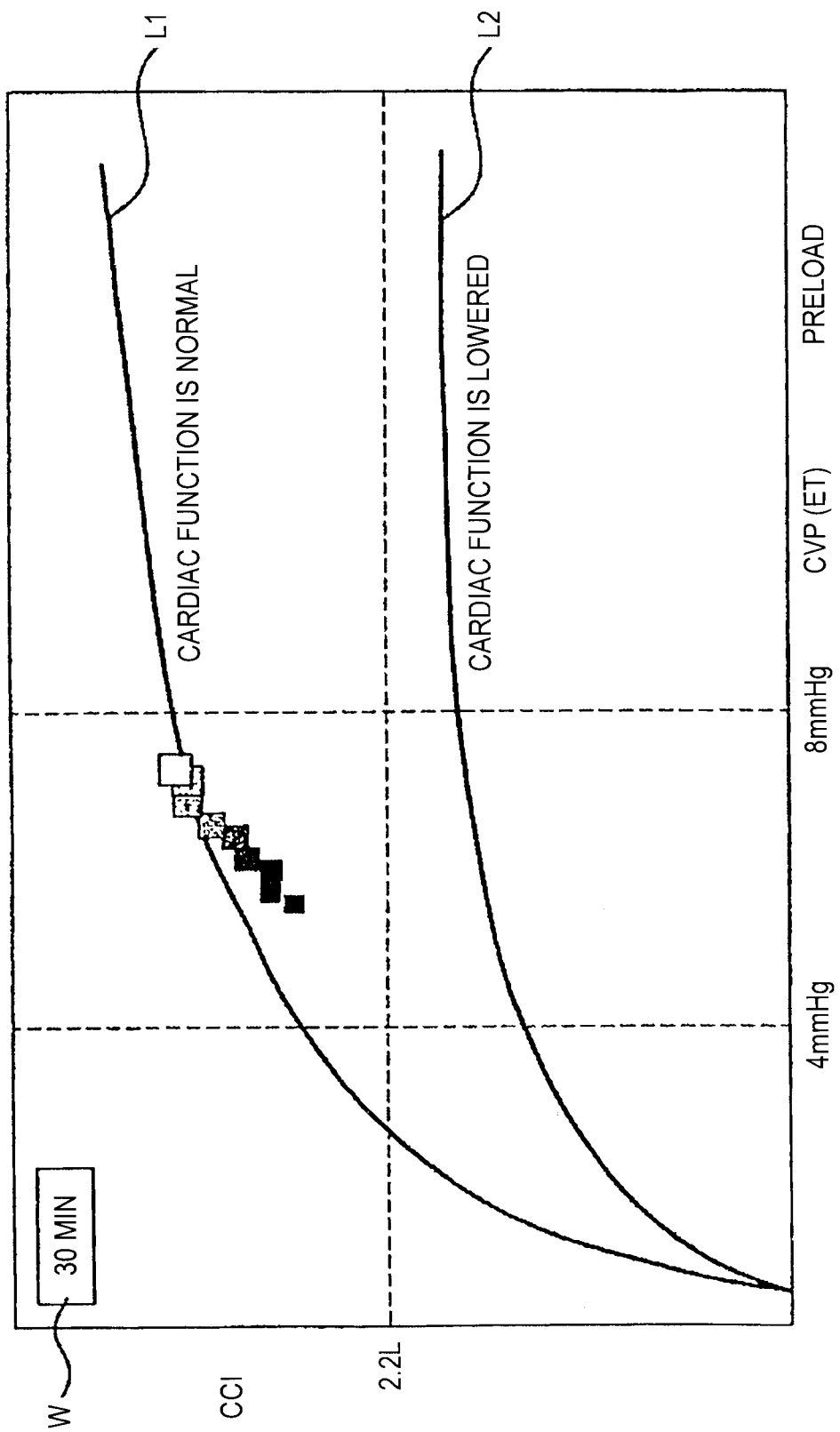
FIG. 3 is a view showing another example of an image which is displayed in the embodiment of the biological parameter displaying apparatus of the invention.

Hereinafter, an embodiment of the biological parameter displaying apparatus of the invention will be described with reference to the accompanying drawings. In the figures, the identical components are denoted by the same reference numerals, and duplicated description will be omitted. As shown in FIG. 1, the biological parameter displaying apparatus includes a first measuring unit 11 and a second measuring unit 12.

As the first measuring unit 11 and the second measuring unit 12, a blood pressure measuring unit which measures an invasive blood pressure such as the central venous pressure (CVP), the pulmonary arterial pressure (PAP), the pulmonary arterial wedge pressure (PCWP), the arterial pressure (ART), and the intracardiac pressure (RAP, RVP, LAP, LVP), a cardiac output measuring unit which measures the cardiac output CO indicating the amount of blood pumped out from the heart for one minute, or a measuring unit which can measure the preload and afterload of the heart, such as the CVP-ET or the PPV is preferable. The measuring units are not limited to these units, and may be any measuring unit as far as it can acquire a measurement value which is equivalent to or reflects a biological parameter. Particularly, measuring units which can continuously measure the biological parameters are preferred. Usually, these biological parameters are often measured by an invasive technique. Alternatively, the biological parameters may be measured by a noninvasive technique. Anyway, the first measuring unit 11 and the second measuring unit 12 are requested to be different measuring units.

Here, the preload means the amount of blood which maintains the ventricle and the lumen of a large blood vessel before the cardiac contraction (the end-diastole time). The term of CVP-ET is a value which is acquired by measuring the central venous pressure (CVP) at the timing of the end-tidal, and used as an index of the preload of the right ventricle. The details are disclosed in JP-A-2010-200901. The term of PPV means the respiratory variation of the pulse pressure, and is the variation of the pulse pressure (the difference between the systolic blood pressure and the diastolic blood pressure) which is acquired by performing calculation on the pulse pressure, and used as an index of the preload of the right ventricle.

The signals acquired in the above-described various sensors are processed, and then sent to a CPU 30.

The CPU 30 includes a coordinate displaying unit 31, a plot data producing unit 32, a plot displaying unit 33, a determination criterion displaying unit 34, and a region displaying unit 35.

An inputting unit 50 configured by a touch panel, a keyboard, and the like is connected to the CPU 30. Through the inputting unit 50, two kinds of biological parameters which are to be plotted and displayed in XY coordinates are selected from biological parameters which are measured by the measuring units. In the embodiment, the interval (time zone) between data can be selected from 1 m, 10 m, 30 m, 1 h, and 4 h. Through the inputting unit 50, it is possible also to select whether a trend display or a plot display in the XY coordinates is to be performed. It is a matter of course that the numbers are not limited to the above.

The coordinate displaying unit 31 of the CPU 30 draws a graph using XY coordinates in which data which are measured by the first measuring unit 11, and which are related to a first biological parameter are set as the X-axis, and data which are measured by the second measuring unit 12, and which are related to a second biological parameter are set as the Y-axis, on a displaying unit 40.

The plot data producing unit 32 produces plot data based on measurement values of the first biological parameter and the second biological parameter which are measured at the same time or in the same time zone by the first measuring unit 11 and the second measuring unit 12. The produced plot data are plotted in the XY coordinates by the plot displaying unit 33. The fact that the measurement values are measured at the same time or in the same time zone is detected based on the input times of the data in the case of real-time measurement. In the case of not real-time measurement, the CPU 30 acquires the measurement start times and the sampling intervals of the data, and the detection is performed based on these data. The plotting interval is an interval which is set through the inputting unit 50. The value of the plotting interval is displayed in a region W of a screen shown in FIGS. 2 to 6. Alternatively, the plotting may be performed in a manner showing the time sequence which will be described later.

The term "at the same time" means the time relationship in the case where the plot data producing unit 32 produces plot data based on measurement values which are measured at the same time by the first measuring unit 11 and the second measuring unit 12, and includes the time relationship in the case where plot data are produced based on two measurement values which are not measured at the same time, but in which the measurement time by the first measuring unit 11 and that by the second measuring unit 12 are closest to each other, or latest measurement values which are measured by the respective measuring units.

In the case where the plot displaying unit 33 performs plotting while biological parameters are measured in real time, it is preferable to perform the plotting base on two data which are measured by the first measuring unit 11 and the second measuring unit 12 at times that are closest to each other.

The term "in the same time zone" means the time relationship in the case where representative values are acquired from groups of measurement values of the measured biological parameters in a predetermined time period immediately before the plotting, and the plot data producing unit 32 produces plot data based on the representative values. Examples of the representative value are the mode, mean, and median values of a measurement value group of each biological parameter.

As described above, the plot data producing unit 32 produces plot data based on the representative values acquired from measurement values which are measured at the same time by the first measuring unit 11 and the second measuring unit 12. The term "the representative values acquired from measurement values which are measured at the same time by the first measuring unit 11 and the second measuring unit 12" means that, in the case where each of the measuring units samples measurement values at intervals of 1 second, for example, the mode, mean, or median value which is acquired from a group of 60 measurement values that are measured from 11 o'clock to 11 o'clock 1 minute is set as plot data of 11 o'clock.

Alternatively, the term "in the same time zone" may mean the time relationship in the case where the plot data producing unit 32 produces plot data by using a mathematical technique such as the mode, mean, and median values of a measurement value group of biological parameters measured between the plotted intervals (above-described data intervals).

As the manner showing the time sequence, a configuration where the brightness is changed by a predetermined gradation in the unit of the elapsed time of data, that where arrows or lines are used, that where the color is gradually changed, and that where the shape or size of a plot point is changed may be used singly or combinedly. In order that data can be traced time-sequentially, in addition to or separately from the above-described manner, an image may be produced so that several sequential plot points have an adequate size and overlapped with one another, or are not overlapped with one another but made close to one another, or plot points are connected to one another by arrows or lines. These display manners are shown in FIGS. 2 to 6, and 9A to 9D.

Figure 9A:
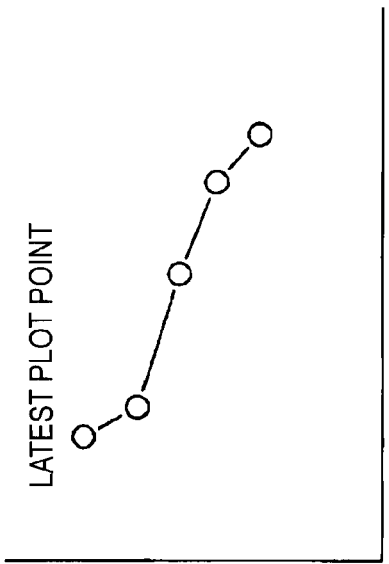
FIGS. 9A to 9D are views showing still further examples of an image which is displayed in the embodiment of the biological parameter displaying apparatus of the invention, and in which plots are connected to one another by lines.
Figure 9C:
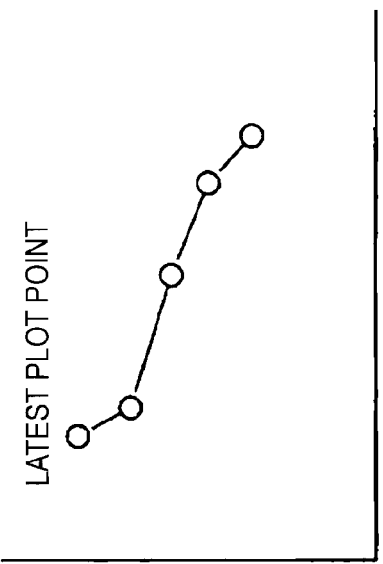
Figure 9B:
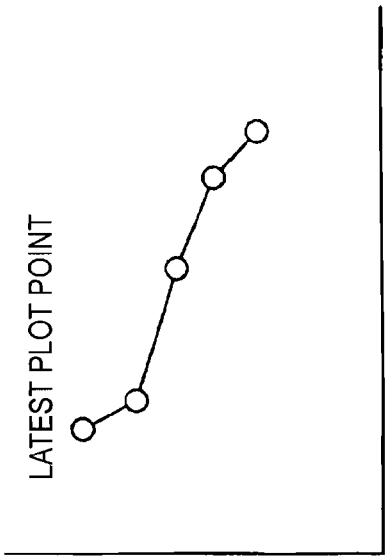
Figure 9D:
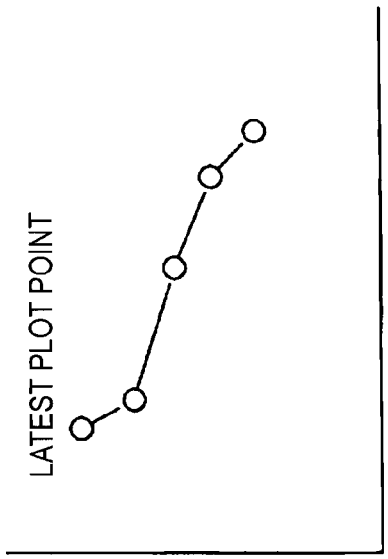

Examples of the display manner are shown in FIGS. 9A to 9D. FIG. 9A shows a display manner in which both ends of a line connecting plot points are contacted with the plot points, respectively. FIG. 9B shows a display manner in which both ends of a line connecting plot points are not contacted with the plot points. FIGS. 9C and 9D show display manners in which one end of a line connecting plot points is contacted with one of the plot points.

In order that the latest plot is clearly shown, in addition to or separately from the above-described manner, the plotted shape is made different from that of other plot points (for example, the latest plot point is triangular, and other plot points are circular). Alternatively, the latest plot point may blink. In the case where a plurality of data are close to and are overlapped with one another, a newer plot point may be displayed in a more front face.

The CPU 30 further includes the determination criterion displaying unit 34. The determination criterion displaying unit 34 displays information (for example, previously stored in accordance with two kinds of biological parameters which are to be plotted and displayed in the XY coordinates) indicating whether a plot point is normal or abnormal as the state of a living body, in the coordinates. Specific examples of the information are curves L1, L2 shown in FIGS. 2 and 3. In the case where the cardiac function is normal, the cardiac function traces the locus such as the curve L1, and, in the case where the cardiac function is abnormal, the cardiac function traces the locus such as the curve L2. When plot points and the curves L1, L2 are displayed together, therefore, it is possible to easily know the state of the cardiac function of a living body.

Figure 4:
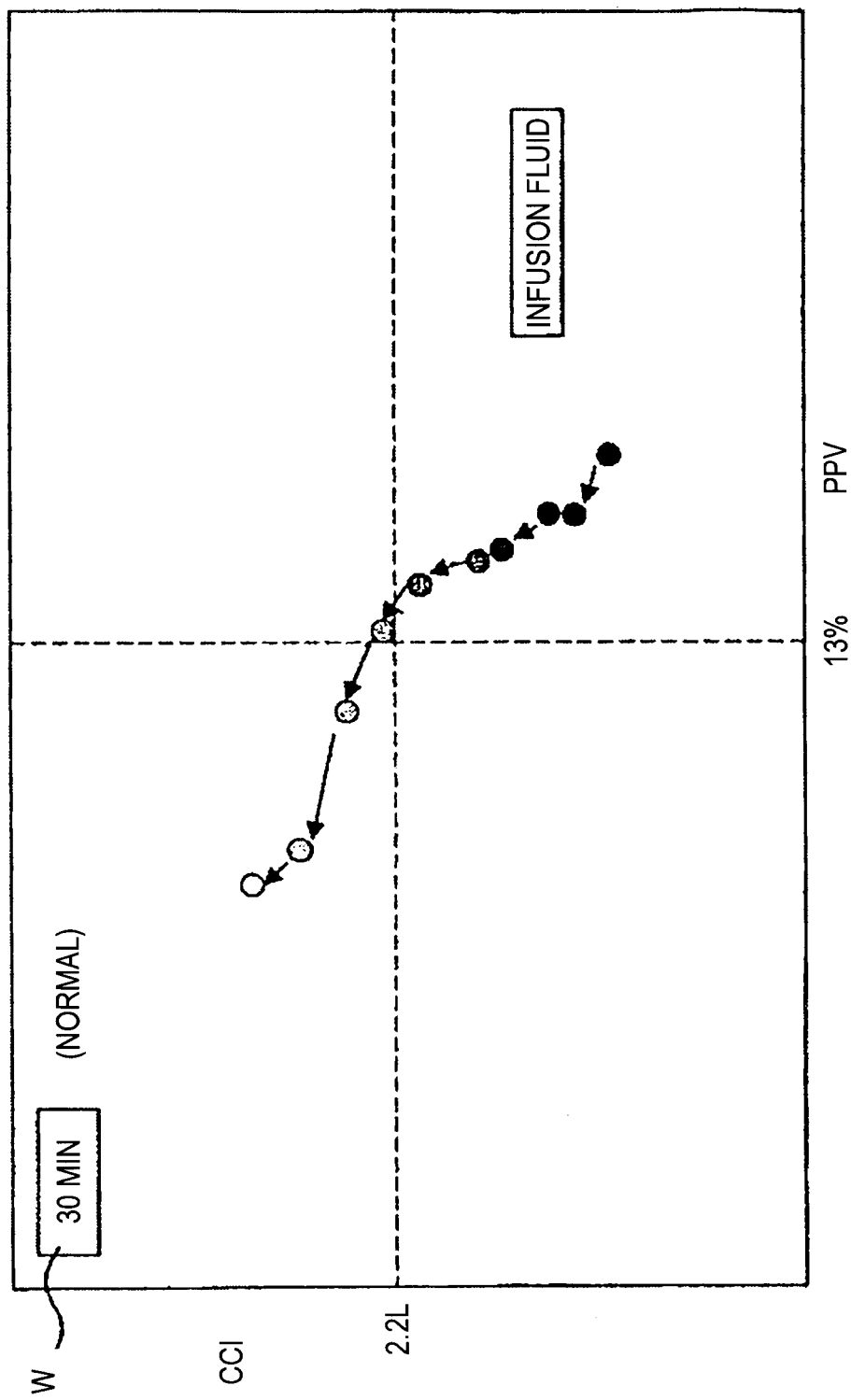
FIG. 4 is a view showing a further example of an image which is displayed in the embodiment of the biological parameter displaying apparatus of the invention.

In the case where the biological parameters of the ordinate and the abscissa are changed, the determination criterion displaying unit 34 displays a plot point correspondingly with the change in a display manner in which, as shown in FIG. 4, the time sequence is clearly shown in the XY coordinates in accordance with data of two kinds of biological parameters. Also in this case, the determination criterion displaying unit 34 may display information (for example, a line which is different from FIG. 3) indicating whether a plot point in the biological parameter of FIG. 4 is normal or abnormal as the state of a living body.

Figure 5:
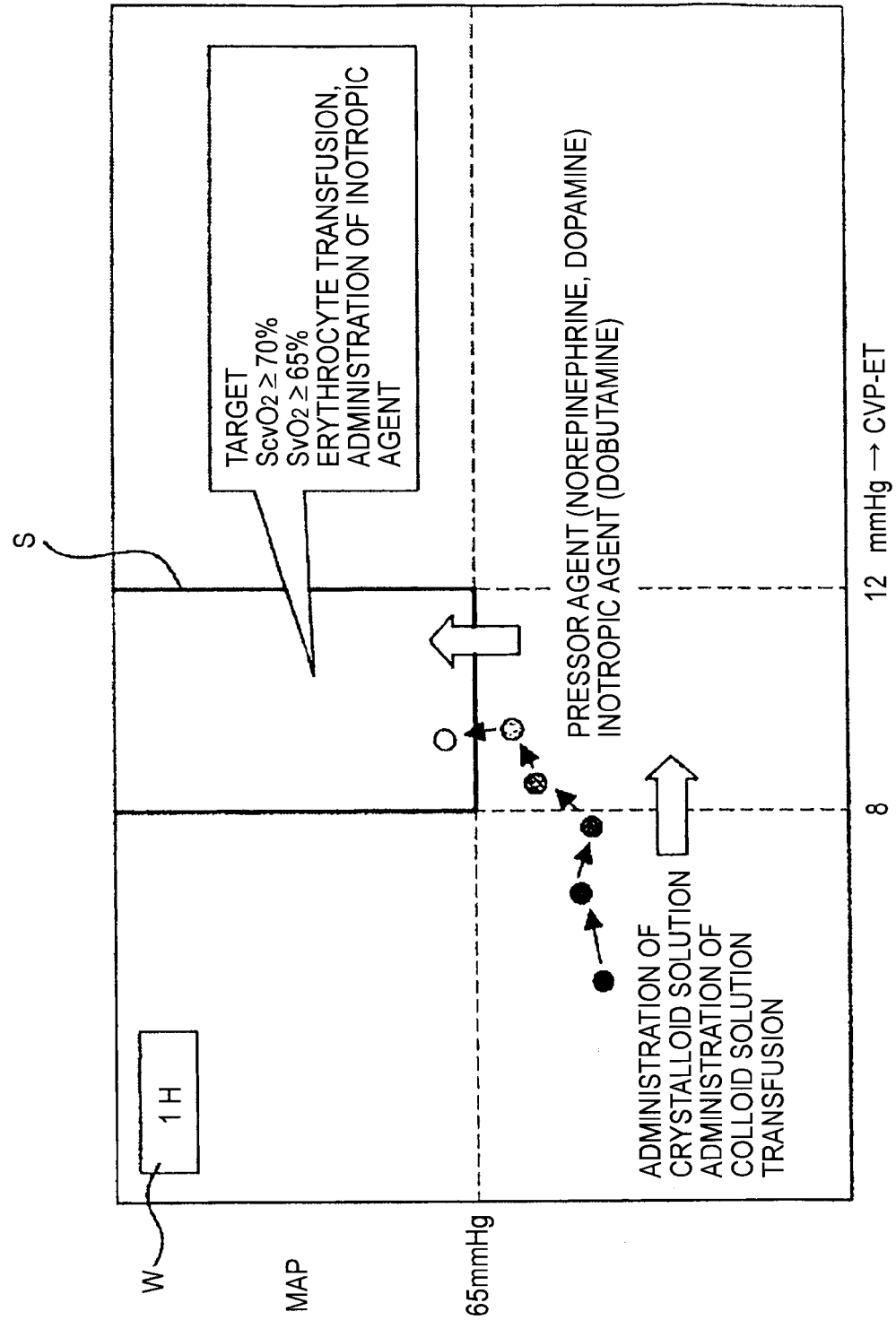
FIG. 5 is a view showing a still further example of an image which is displayed in the embodiment of the biological parameter displaying apparatus of the invention.

The CPU 30 further includes the region displaying unit 35. The region displaying unit 35 displays a region (for example, previously stored in accordance with two kinds of biological parameters which are to be plotted and displayed in the XY coordinates) where a plot point in the coordinates is normal as the state of a living body, as shown in FIG. 5 so as to be clearly distinguished from another region. In order to clearly distinguish the region, any display manner such as that in which the region is boxed, or that in which the color of a normal region is different from that of another region may be employed as far as a normal region is clearly known.

Preferably, the settings related to the determination criterion displaying unit 34 and the region displaying unit 35 may be freely set in consideration of the individual differences, the operation of the facility, and the like.

Referring to FIG. 5, in order to enable a medical person to a perform a procedure so that a plot point of biological parameter data enters the range enclosed by a rectangular frame S in which the MAP is 65 mmHg or higher and the CVP-ET is from 8 mmHg to 12 mmHg, various medical procedures or the like to be performed may be displayed.

As the range, the EGDT (Early Goal Direct Therapy) which is a guideline that is to be achieved in a patient with severe septicemia or septic shock within six hours after initial treatment in order to normalize the circulatory dynamics and improve tissular hypoxia is exemplified. However, the range is not limited to this.

Figure 6:
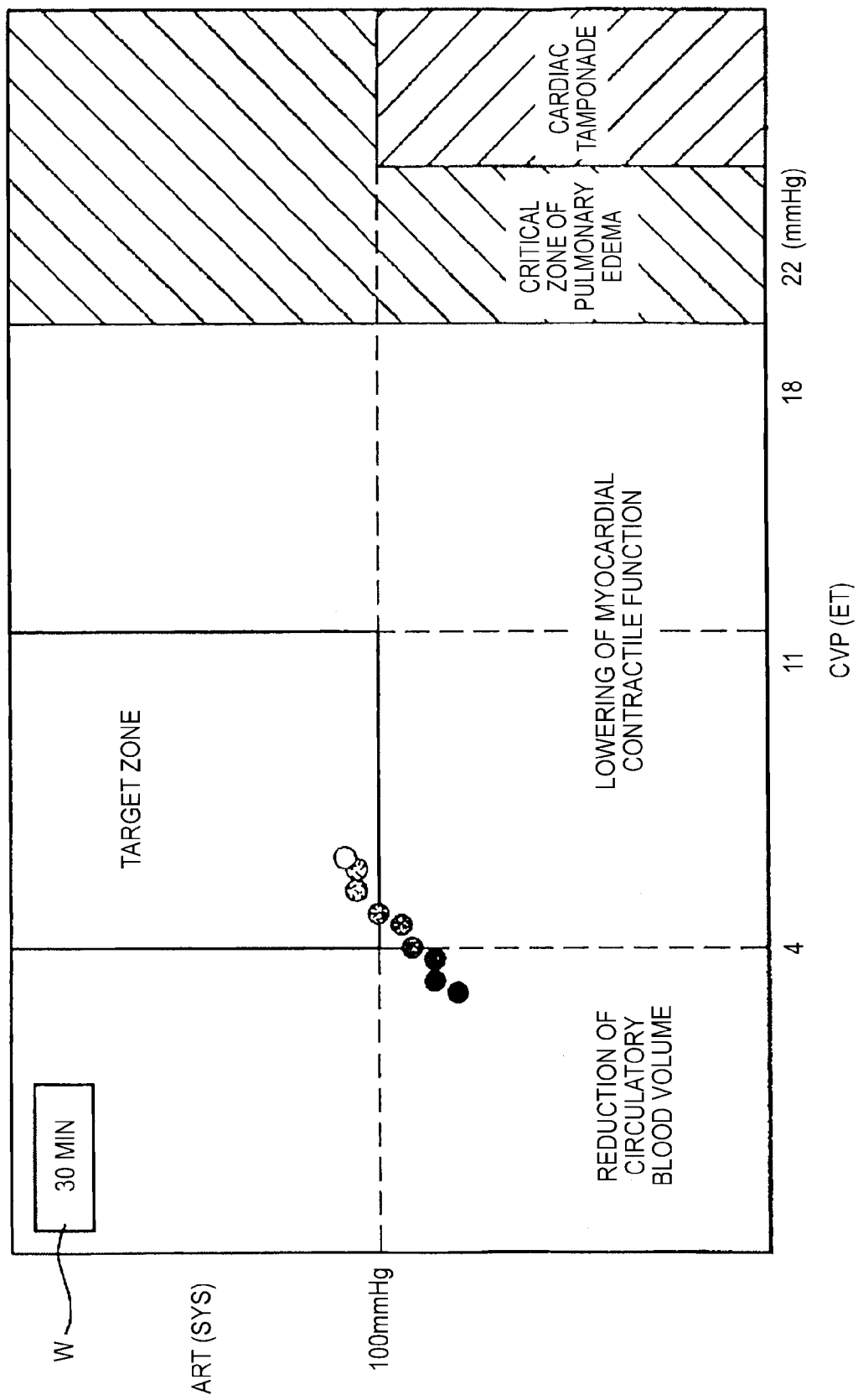
FIG. 6 is a view showing a still further example of an image which is displayed in the embodiment of the biological parameter displaying apparatus of the invention.
Figure 7:
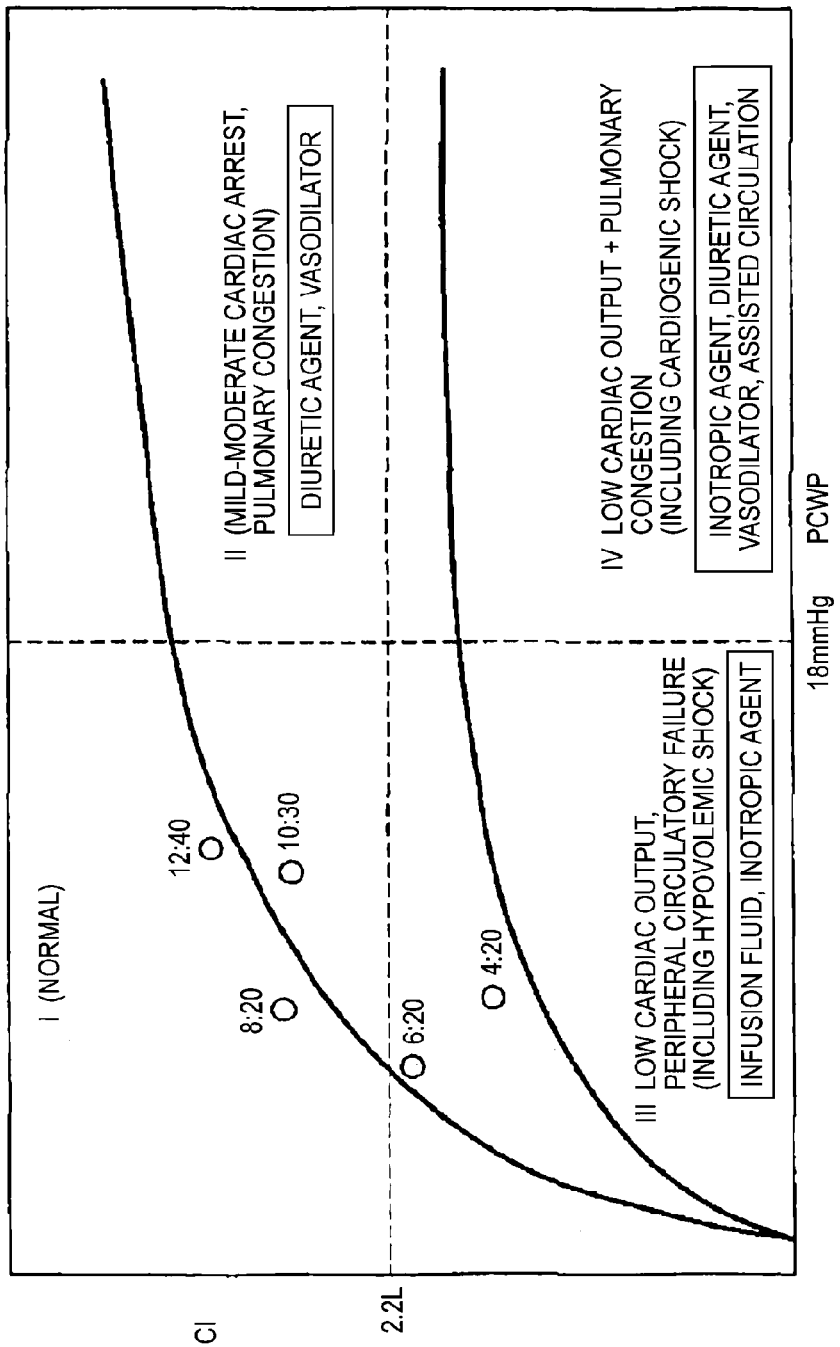
FIG. 7 is a view showing an example of the Forrester classification.
Figure 8:
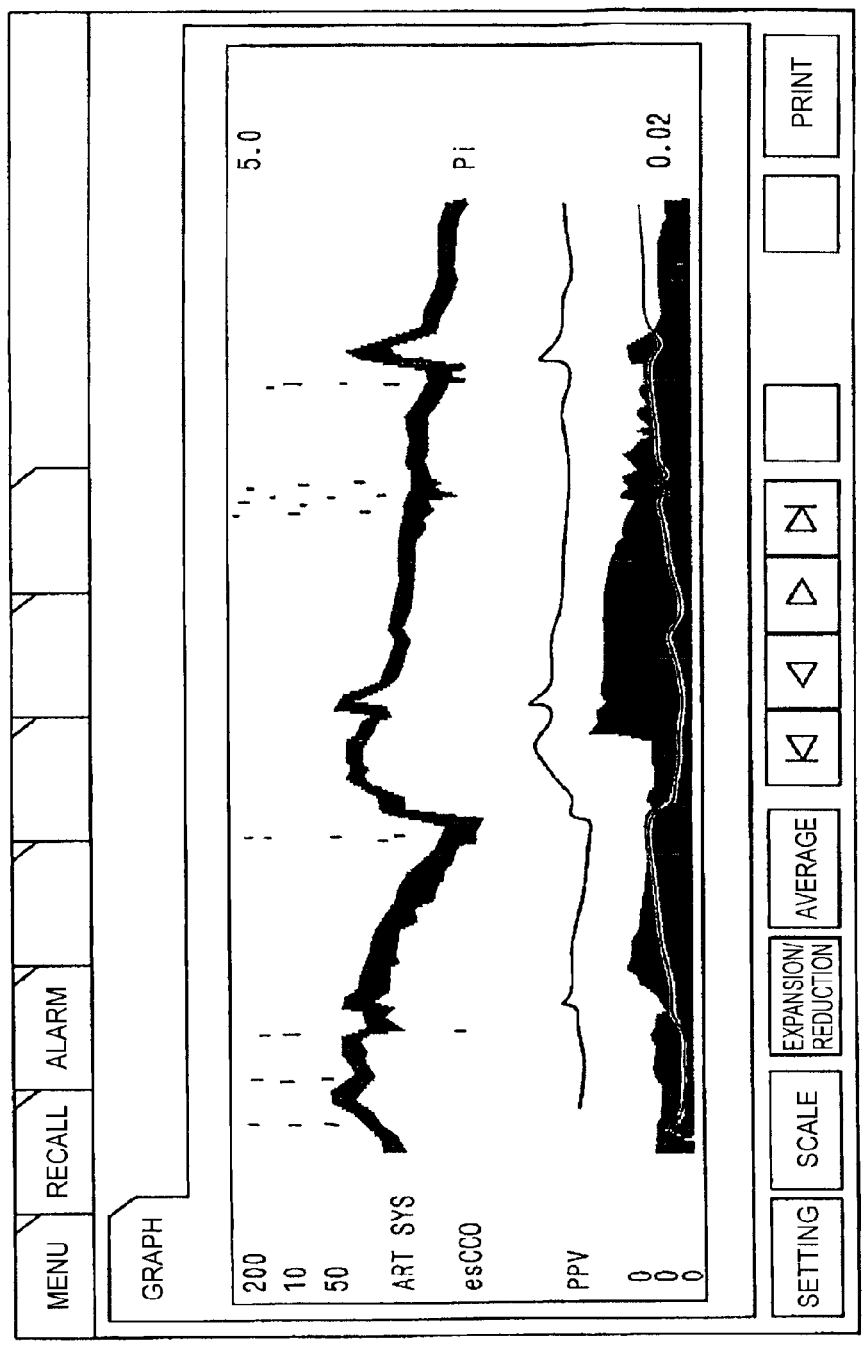
FIG. 8 is a view showing an example of a trend display displayed in a related-art biological parameter displaying apparatus.

In the range, as shown in FIG. 6, the region displaying unit 35 may divide the coordinate into a plurality of regions such as "Target zone", "Reduction of circulatory blood volume", "Lowering of myocardial contractile function", "Critical zone of pulmonary edema", and "Cardiac tamponade". In this case, more preferably, "Target zone" which is normal as the state of a living body, and other particularly critical regions such as "Cardiac tamponade" and "Critical zone of pulmonary edema" may be displayed in different display manners. Although, in FIG. 6, the critical regions are made distinguishable by right and left slanting hatchings, the regions may be displayed so as to be clearly distinguishable from other regions. An adequate manner such as that in which the region is boxed, or that in which the color of the region is different from that of other regions may be employed.

The displaying unit 40 is configured by, for example, an LCD which displays information supplied from the coordinate displaying unit 31, plot displaying unit 33, determination criterion displaying unit 34, and region displaying unit 35 of the CPU 30.

The biological parameter displaying apparatus of the invention may be used not only in a so-called bedside biological information monitoring apparatus but also in a station type biological information monitoring apparatus (central monitor) which receives and displays biological information of patients transmitted from a plurality of bedside biological information monitoring apparatuses. In this case, the biological information displaying apparatus plots information transmitted from the bedside biological information monitoring apparatuses, in coordinates, whereby the living body states of a plurality of patients can be simultaneously displayed. In the case where a plurality of patients are simultaneously displayed, it is preferred to perform the display while the color, shape, and the like of a plot are changed for each patient.

Figure 10:
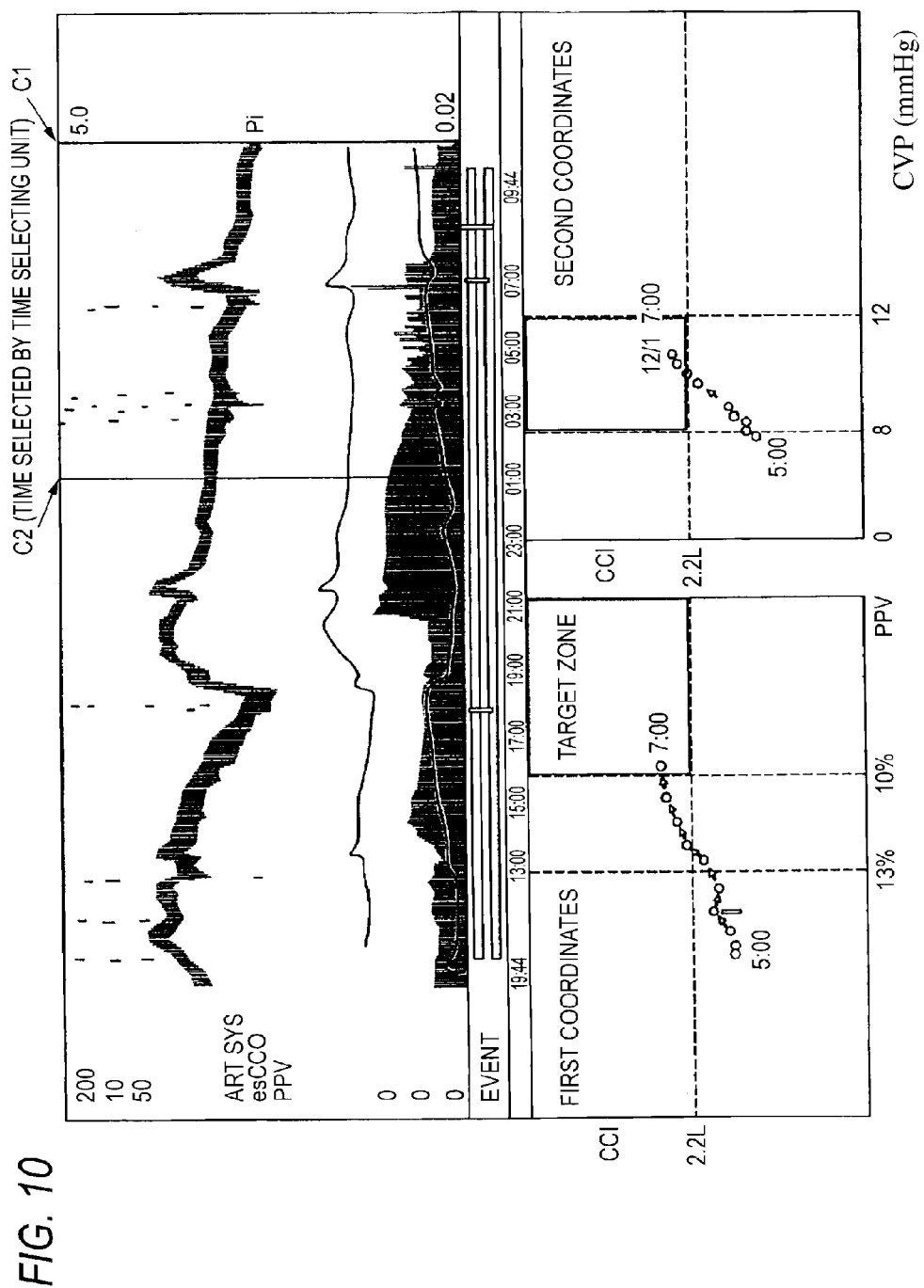
FIG. 10 is a view showing a still further example of an image which is displayed in the embodiment of the biological parameter displaying apparatus of the invention, and in which a plurality of coordinates are displayed on a screen and the time which is selected.

FIG. 10 shows an example of the display by the biological parameter displaying apparatus. In the upper side of FIG. 10, a trend display is displayed, and, in the lower side, a plurality of coordinates are displayed by the plot displaying unit 33.

A cursor C1 which is at the right end of the trend display of FIG. 10 is used for displaying values of biological parameters such as the ART and the PPV at the present time. The biological parameter displaying apparatus includes a time selecting unit through which the user can perform operations such as that a dedicated cursor C2 (in the vicinity of the middle of the trend display of FIG. 10) is set to data of the time of concern in the trend display of FIG. 10, that (although not illustrated) trend data of the time of concern is clicked, and that the time of concern is directly input. The plot displaying unit 33 displays plot data corresponding to the time which is selected by the time selecting unit, in at least one of the first and second coordinates. The displayed plot data corresponding to the selected time may be one data or plural number of data.

The coordinates in the lower side of FIG. 10 are examples of the first and second coordinates, and show that the plot data corresponding to the time which is selected by the time selecting unit can be replayed and displayed. The term "corresponding to the time which is selected" means that times in the neighborhood of the selected time. Preferably, the user can freely perform the setting related to the range (time duration) of the neighborhood times.

In the left coordinates of the lower side of FIG. 10, plot data based on biological data are plotted and displayed while the ordinate indicates the CCI (Continuation Cardiac Index) and the abscissa indicates the PPV (Pulse Pressure Variation), and, in the right coordinates of the lower side of FIG. 10, plot data based on biological data are plotted and displayed while the ordinate indicates the CCI and the abscissa indicates the CVP. In FIG. 10, the example in which the ordinates indicate the same biological parameter or the CCI is shown. Alternatively, the abscissas may indicate the same biological parameter, or the ordinates and the abscissas may indicate different biological parameters, respectively.

For example, the abscissa in the left coordinates of the lower side of FIG. 10 indicates the PPV. The PPV suitably reflects the response to infusion fluid administered to the patient, and hence can be used as an index for administration of infusion fluid. Moreover, the abscissa in the right coordinates of the lower side of FIG. 10 indicates the CVP. The CVP can be used as an index for determining whether the amount of administered infusion fluid is adequate or not. Therefore, it is seen that, when a plurality of coordinates are displayed for one patient as shown in the lower side of FIG. 10, the circulatory dynamics can be known more accurately, and infusion fluid management can be effectively known. The biological parameter displaying apparatus of the embodiment includes the configuration for performing such a display.

According to an aspect of the invention, data related to two different biological parameters that are measured at the same time or in the same time zone are automatically plotted in XY coordinates. Therefore, the apparatus is preferred in the case where the process (particularly, the circulatory dynamics) of the state of a living body is to be known easily and adequately.

According to an aspect of the invention, plot data are produced based on one of the median, mean, and mode values of the group of measurement values which are measured in the same time zone. Even when a sudden noise enters the measurement value, therefore, an influence on data to be plotted can be reduced or eliminated, and stable and accurate data are plotted.

According to an aspect of the invention, plotting is performed in a manner showing the time sequence, such as that in which the brightness, size, color, or shape of the most recent plot data is different from that of other data, or that in which the most recent plot data blink. Therefore, plotted data can be traced time-sequentially, and hence the latest state of a living body can be easily known.

According to an aspect of the invention, in the case where data are separated from one another, the displayed data can be traced time-sequentially, and hence the latest state of a living body can be easily known. In the case where data are close to one another, moreover, the arrows or the lines are not displayed, and the display is prevented from being hardly viewed.

According to an aspect of the invention, in the case where a plurality of data overlap one another in the coordinates, the plot point which is latest in the time sequence is displayed on the front. Therefore, the latest state of a living body can be easily known.

According to an aspect of the invention, information indicating normality or abnormality, and an adequate or critical region are displayed in the coordinates. Therefore, it is possible to easily know whether the state of a living body is normal or abnormal.

According to an aspect of the invention, data of a plurality of persons can be simultaneously plotted in the coordinates. Therefore, living body states of a plurality of persons can be simultaneously known, and the working efficiency of a medical person related to a monitoring operation is improved.

According to an aspect of the invention, the first coordinates and the second coordinates can be simultaneously displayed. Therefore, the circulatory dynamics can be known more accurately, and adequate infusion fluid management can be realized.

According to an aspect of the invention, plot data at the time which is desired by the user, can be replayed in the coordinates. Therefore, oversight or the like can be prevented from occurring.

What is claimed is:

1. A cardiac parameter displaying apparatus comprising:
a coordinate displaying unit which displays first coordinates in which a first cardiac parameter of a patient, which is measured by a first measuring unit, is set as an X-axis, and a second cardiac parameter of the patient, which is different in kind from the first cardiac parameter and which is measured by a second measuring unit, is set as a Y-axis;
a plot data producing unit which produces first plot data, each of the first plot data being produced based on first measurement values of the first and second cardiac parameters which are measured at a same time or in a same time zone, the first measurement values of the first and second cardiac parameters being representative values of the first and second cardiac parameters, which are acquired from groups of values of the first and second cardiac parameters measured at the same time or in the same time zone;
a plot displaying unit which plots the first plot data in the first coordinates
a region displaying unit which displays a plurality of regions showing whether the first plot data are normal or critical as a state of the patient,
wherein the first plot data includes at least two data including first data and second data, the first data is subsequent to the second data, the first data and the second data are displayed at a time interval, and the time interval is set in advance,
wherein the representative values are one of median, mean, and mode values of the groups of the values of the first and second cardiac parameters measured at the same time or in the same time zone,
wherein the plurality of regions include a normal region corresponding to a normal state of the patient and a critical region corresponding to a critical state of the patient,
wherein the critical region is divided into a plurality of sub-regions which are distinguished from each other based on a condition of the patient,
wherein the first cardiac parameter indicates a cardiac output/cardiac function which can be continuously measured or a preload/afterload of a heart which can be continuously measured, and
wherein the second cardiac parameter indicates the other of the cardiac output/cardiac function which can be continuously measured and the preload/afterload of a heart which can be continuously measured.

2. The biological parameter displaying apparatus according to claim 1, wherein the first plot data are plotted in a manner showing a time sequence, and, in the manner showing the time sequence, location and appearance of the first data are different from location and appearance of the second data.

3. The cardiac parameter displaying apparatus according to claim 2, wherein the first plot data include first, second and third data,
   the second data is subsequent to the third data, and the first data is subsequent to the second data and is a latest data, and
   in the manner showing the time sequence, a brightness of the first data is highest, and a brightness of the second data is identical to a brightness of the third data or a brightness of the second data is higher than a brightness of the third data.

4. The cardiac parameter displaying apparatus according to claim 2, wherein the first plot data include first, second and third data,
   the second data is subsequent to the third data, and the first data is subsequent to the second data and is a latest data, and
   in the manner showing the time sequence, a size of the first data is largest, and a size of the second data is identical to a size of the third data or a size of the second data is larger than a size of the third data.

5. The cardiac parameter displaying apparatus according to claim 2, wherein
   in the manner showing the time sequence, a color of the first data is different from a color of the second data.

6. The cardiac parameter displaying apparatus according to claim 2, wherein
   in the manner showing the time sequence, the first data and the second data are connected to each other by an arrow or a line.

7. The cardiac parameter displaying apparatus according to claim 6, wherein when a distance between the first data and the second data is shorter than a length, the first data and the second data are not connected to each other by the arrow or the line.

8. The cardiac parameter displaying apparatus according to claim 2, wherein the first data is a latest data, and
   in the manner showing the time sequence, a shape of the first data is different from a shape of the second data.

9. The cardiac parameter displaying apparatus according to claim 2, wherein
   the first data is a latest data, and
   in the manner showing the time sequence, the first data blinks and the second data does not blink.

10. The cardiac parameter displaying apparatus according to claim 2, wherein in the manner showing the time sequence, when the first data and the second data are overlapped with each other at least in part, the first data is displayed on the second data.

11. The cardiac parameter displaying apparatus according to claim 1, further comprising a determination criterion displaying unit which displays information indicating whether the first plot data are normal or abnormal as a state of the patient.

12. The cardiac parameter displaying apparatus according to claim 1, wherein the patient includes a plurality of patients.

13. The cardiac parameter displaying apparatus according to claim 1, further comprising a time selecting unit which selects a time, wherein the first plot data corresponding to the selected time are plotted.

14. The cardiac parameter displaying apparatus according to claim 1, wherein the coordinate displaying unit displays second coordinates in which a third cardiac parameter, which is measured by a third measuring unit, is set as an X-axis, and the second cardiac parameter is set as a Y-axis,
   the plot data producing unit produces second plot data, each of the second plot data being produced based on second measurement values of the second and third cardiac parameters which are measured at a same time or in a same time zone, and
   the plot displaying unit plots the second plot data in the second coordinates.

15. The cardiac parameter displaying apparatus according to claim 1, wherein the coordinate displaying unit displays second coordinates in which a third cardiac parameter, which is measured by a third measuring unit, is set as an X-axis, and a fourth cardiac parameter, which is measured by a fourth measuring unit, is set as a Y-axis,
   the plot data producing unit produces second plot data, each of the second plot data being produced based on second measurement values of the third and fourth cardiac parameters which are measured at a same time or in a same time zone, and
   the plot displaying unit plots the second plot data in the second coordinates.

16. The biological parameter displaying apparatus according to claim 1, wherein the time interval is selected from a plurality of candidate times which are set in advance.

17. The cardiac parameter displaying apparatus according to claim 1, wherein the first data is a latest data.

* * * * *